: 5,201,215
: Apr. 13, 1993

[54] METHOD FOR SIMULTANEOUS MEASUREMENT OF MASS LOADING AND FLUID PROPERTY CHANGES USING A QUARTZ CRYSTAL MICROBALANCE

[75] Inventors: Victoria E. Granstaff; Stephen J. Martin, both of Albuquerque, N. Mex.

[73] Assignee: The United States of America as represented by the United States Department of Energy, Washington, D.C.

[21] Appl. No.: 779,727

[22] Filed: Oct. 17, 1991

[51] Int. Cl.$^5$ .............................. G01N 11/00
[52] U.S. Cl. ................... 73/54.41; 73/32 A; 73/579
[58] Field of Search ............... 73/53, 54, 61 R, 62.1, 73/32 A, 579, 59; 310/316, 364; 177/210 R, 210 FP

[56] References Cited

U.S. PATENT DOCUMENTS

| | | | |
|---|---|---|---|
| 3,934,059 | 1/1976 | Polinsky | 437/246 |
| 4,311,725 | 1/1982 | Holland | 427/10 |
| 4,391,338 | 7/1983 | Patashnick et al. | 177/210 |
| 4,477,418 | 10/1984 | Mullhaupt et al. | 423/219 |
| 4,561,286 | 12/1985 | Sekler et al. | 73/24.06 |
| 4,721,874 | 1/1988 | Emmert | 73/54 X |
| 4,741,200 | 5/1988 | Hammerle | 73/54 |
| 4,754,640 | 7/1988 | Fitzgerald et al. | 73/54 |
| 4,783,987 | 11/1988 | Hager et al. | 73/54 X |
| 4,788,466 | 11/1988 | Paul | 310/316 |
| 4,862,384 | 8/1989 | Bujard | 73/54 X |
| 4,917,499 | 4/1990 | Champetier et al. | 374/14 |
| 4,999,284 | 3/1991 | Ward | 435/4 |

OTHER PUBLICATIONS

K. K. Kanazawa et al., "Evaluation of a Real-Time Rate Monitor For Electroless Nickel Deposition", *Plating and Surface Finishing* Jul. 1987, pp. 52–55.
K. Kanazawa et al., "The Oscillation Frequency of a Quartz Resonator in Contact with a Liquid," *Analytical Chemica Acta*, 1985, vol. 175, pp. 99–105.
G. Sauerbrey, "Verwendung con Schwingquarzen zur Wagung dunner Schichten und zur Mikrowagung," *Zeitschrift fur Physik*, 1959, vol. 155, pp. 206–222.
Lu et al. "Investigation of Film-thickness by Oscillating Quartz Resonators with Large Mass Load," *J. Appl. Phys.*, Nov. 1972 vol. 43, No. 11, 4385–4390.
Namura et al. *Nippon Kagaku Kaishi*, 1980, p. 1121.
R. Schumacher, "The Quartz Microbalance: A Novel Approach to the In-Situ Investigation of Interfacial Phenomena at the Solid/Liquid Junction," *Angew. Chem. Int. Ed. Engl.*, Apr. 1990, vol. 29, No. 4, pp. 329–343.
M. R. Deakin et al., "Prussian Blue Coated Quartz Crystal Microbalance as a Detector for Electroinactive Cations in Aqueous Solution," 1989, Anal. Chem., vol. 61, pp. 290–295.
M. Thompson et al. "Liquid-Phase Piezoelectric and Acoustic Transmission Studies of Interfacial Immunochemistry," *Anal. Chem.*, 1986, vol. 58, pp. 1006–1209.
Konash et al., "Piezoelectric Crystals as Detectors in Liquid Chromatography," Anal. Chem., 1980, vol. 52, pp. 1929–1931.
M. Seo et al., "Study on Corrosion of Copper Thin Film In Air Containing Pollutant Gas by a Quartz Crystal Microbalance," *Extended Abstract—178th Meeting of The Electrochemical Society*, Seattle, Wash. 1990, Abstract No. 187, pp. 272–273.
S. Bruckenstein et al., "An In Situ Weighing Study of the Mechanism for the Formation of the Adsorbed Oxygen Monolayer at a Gold Electrode," *J. Electroanal. Chem.*, 1985, vol. 188, pp. 131–136.
M. D. Ward, "In Situ Interfacial Mass Detection with Piezoelectric Transducers". Science, Aug. 1990, vol. 249, pp. 1000–1007.
K. K. Kanazawa et al., "Frequency of a Quartz Microbalance in Contact with Liquid," Anal. Chem., 1985, vol. 57, pp. 1770–1771.

*Primary Examiner*—Hezron E. Williams
*Assistant Examiner*—Michael J. Brock
*Attorney, Agent, or Firm*—Karla Ojanen; James H. Chafin; William R. Moser

[57] ABSTRACT

A method, using a quartz crystal microbalance, to obtain simultaneous measurement of solid mass accumulation and changes in liquid density-viscosity product. The simultaneous real-time measurements of electrical parameters yields that changes in surface mass can be differentiated from changes in solution properties. Two methods to obtain the admittance/frequency data are employed.

8 Claims, 5 Drawing Sheets

METHOD FOR SIMULTANEOUS MEASUREMENT OF MASS LOADING AND FLUID PROPERTY CHANGES USING A QUARTZ CRYSTAL MICROBALANCE

The U.S. Government has rights in this invention pursuant to Contract No. DE-AC04-76DP00789 between the Department of Energy and American Telephone & Telegraph Company.

BACKGROUND OF THE INVENTION

This invention relates generally to the field of microchemical sensors, and more particularly to using electrical parameters to differentiate changes in surface mass from changes in chemical solution properties using a quartz crystal microbalance.

The quartz crystal microbalance (QCM) is commonly configured with electrodes on both sides of a thin disk of AT-cut quartz. Because of the piezoelectric properties and crystalline orientation of the quartz, the application of a voltage between these electrodes results in a shear deformation of the crystal. The crystal can be electrically excited into resonance when the excitation frequency is such that the crystal thickness is an odd multiple of half the acoustic wavelength. At these frequencies, a standing shear wave is generated across the thickness of the plate for the fundamental and higher harmonic resonances.

QCMs were originally used in vacuo to measure deposition rates. As shown by Sauerbrey, Z. PHYS., Vol. 155, pp. 206-222 (1959), changes in the resonant frequency are simply related to mass accumulated on the crystal, and this teaching has been implemented in U.S. Pat. No. 4,788,466, entitled "Piezoelectric Sensor Q-loss Compensation," to Paul et al., Nov. 29, 1988; and U.S. Pat. No. 4,561,286, entitled "Piezoelectric Contamination Detector," to Sekler et al., Dec. 31, 1985; and U.S. Pat. No. 4,391,338, entitled "Microbalance and Method for Measuring the Mass of Matter Suspended Within a Fluid Medium," to Patashnick et al., Jul. 5, 1983. Lu et al., J. APPL. PHYS.Vol. 43, pp. 4385-4390 (1972) showed that the QCM typically may be used as an instrument in the frequency-control element of an oscillator circuit; a precise microbalance is realized by monitoring changes in oscillation frequency. More recently, QCMs have been shown to operate in contact with fluids by Numura et al., NIPPON KAGAKU KAISHI, pp. 1121(1980) enabling their use as solution phase microbalances. This microbalance capability has facilitated a number of solution measurements, as in, for instance, U.S. Pat. No. 4,741,200, entitled "Method and Apparatus for Measuring Viscosity in a Liquid Utilizing a Piezoelectric Sensor," to Hammerle, May 3, 1988. Other examples include deposition monitoring as taught by Schumacher, ANGEW. CHEM. INT. ED. ENGL., Vol. 29, pp. 329-343 (1990), and U.S. Pat. No. 4,311,725, entitled "Control of Deposition of Thin Films," by Holland, Jan. 19, 1982; species detection by Deakin et al., ANAL. CHEM., Vol. 61, pp. 290-295 (1989); immunoassay by Thompson et al., ANAL. CHEM. Vol. 58, pp. 1206-1209 (1986), and U.S. Pat. No. 4,999,284, entitled "Enzymatically amplified piezoelectric specific binding assay," to Ward et al., Mar. 12, 1991; fluid chromatographic detection shown by Konash et al., ANAL. CHEM., Vol. 52, pp. 1929-1931 (1980); corrosion monitoring by Seo et al., EXTENDED ABSTRACTS—178TH MEETING OF THE ELECTROCHEMICAL SOCIETY, Abstract No. 187, p. 272, Seattle, WA (1990); and electrochemical analysis taught by Bruckenstein et al., J. ELECTROANAL. CHEM., Vol. 188, pp. 131-136 (1988), and by Ward et al., SCIENCE, Vol. 249, pp. 1000-1007 (1990).

Kanazawa et al., ANAL. CHEM., Vol. 57, pp. 1770-1771 (1985), have shown that QCMs operating in solution are also sensitive to the viscosity and density of the contacting solution. Viscous coupling of the fluid medium to the oscillating device surface results in both a decrease in the resonant frequency of the QCM and damping of the resonance.

But, prior to the invention described herein, no one has suggested that the mass and the liquid properties can be measured simultaneously. In fact, no one thought that the measurement of mass loading onto a QCM would be affected by the changes in the density and viscosity of the liquid. Indeed, the prior art assumed the fluid density to be constant. But, because the resonant frequency is affected by both mass and fluid loading, measurement of the resonant frequency alone cannot distinguish changes in surface mass from changes in solution properties. Those of the prior art who measured the viscosity or the density of the fluid simply did not have the means to measure the solid mass accumulation. In fact, their measurement of the fluid properties would be in error if there were any solid mass accumulation on the surface of the QCM. And, those in the prior art measuring solid mass accumulation had to assume that the fluid properties remained constant, otherwise their measurement of mass would be in error. But, in fact, the change in frequency is dependent upon both the mass and the fluid properties, and by measuring specific electrical characteristics over a range of frequencies near resonance, the QCM can differentiate between these loading mechanisms.

It is thus an object of the invention to present a QCM simultaneously loaded by a thin surface mass layer and a viscous fluid. The invention takes advantage of the derived analytical expression for QCM admittance as a function of excitation frequency.

Accordingly, the invention is a method to determine total mass of a solid and/or physical properties of a fluid, both the mass and fluid contacting the same quartz crystal microbalance, comprising applying an oscillating electric field across the thickness of the quartz crystal microbalance in contact with a solid mass interposed between the quartz crystal microbalance and a fluid, then measuring at least one resonant frequency of the quartz crystal microbalance, simultaneously measuring the admittance magnitude at the resonant frequencies, and correlating the resonant frequency and the admittance magnitude to obtain a surface mass density and a fluid viscosity-density product. A second embodiment of the invention comprises applying an oscillating electric field across the thickness of a quartz crystal microbalance, sweeping a frequency over a range that spans at least one resonant frequency of the crystal, measuring the magnitude and phase of the admittance over the frequency range, correlating the admittance data to the frequency, and applying the admittance/frequency correlation to an equivalent circuit model, contacting a solid mass and/or a fluid onto the crystal wherein the solid mass is interposed between the crystal and the fluid, repeating the steps sweeping the frequency range that spans a resonant frequency, measuring the magnitude and phase of the admittance over that frequency range, and correlating the admittance data to the frequency and then applying the admittance/frequency correlation to an equivalent circuit model, and then extracting the solid mass and fluid density-viscosity product from the correlated admittance/frequency data.

DESCRIPTION OF THE INVENTION

Figure 1:
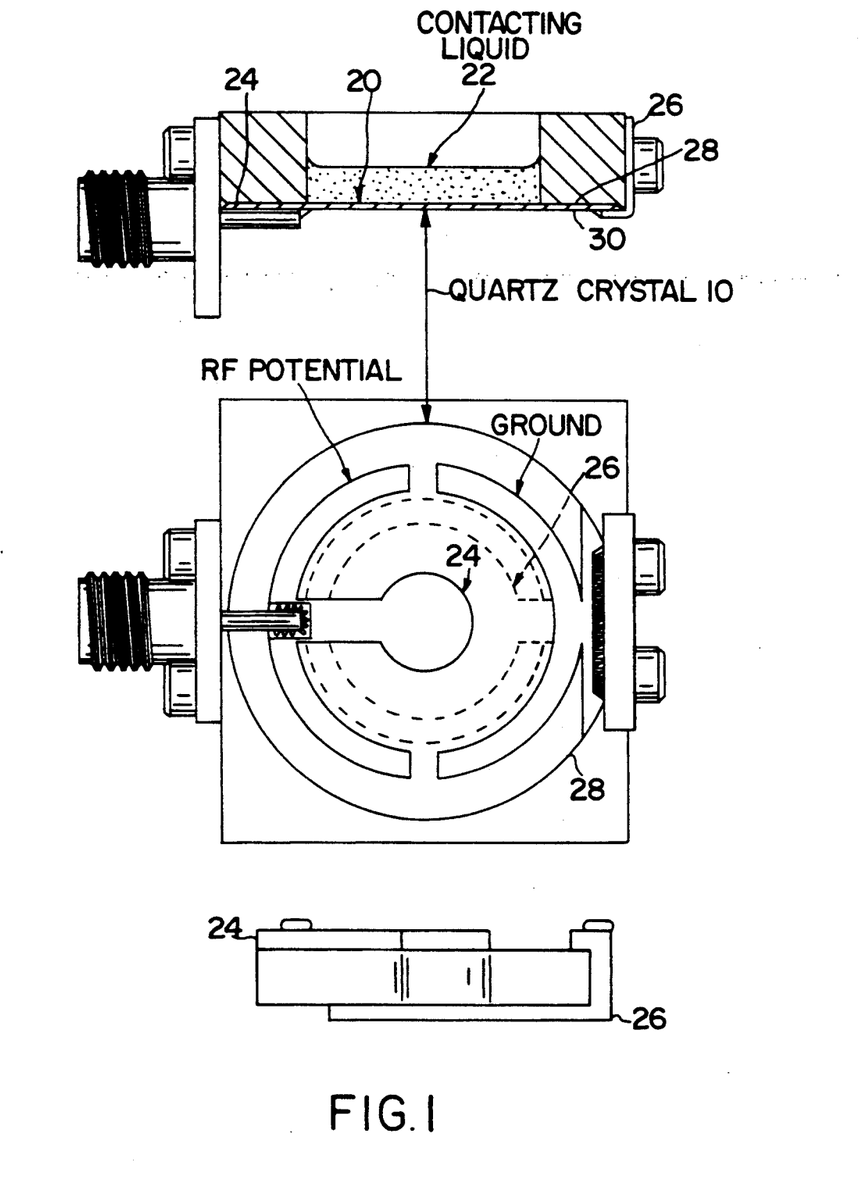
FIG. 1 is a side and bottom view of the test fixture used for electrical admittance measurements of the QCM with a mass layer and/or fluid contacting the device.
Figure 2:
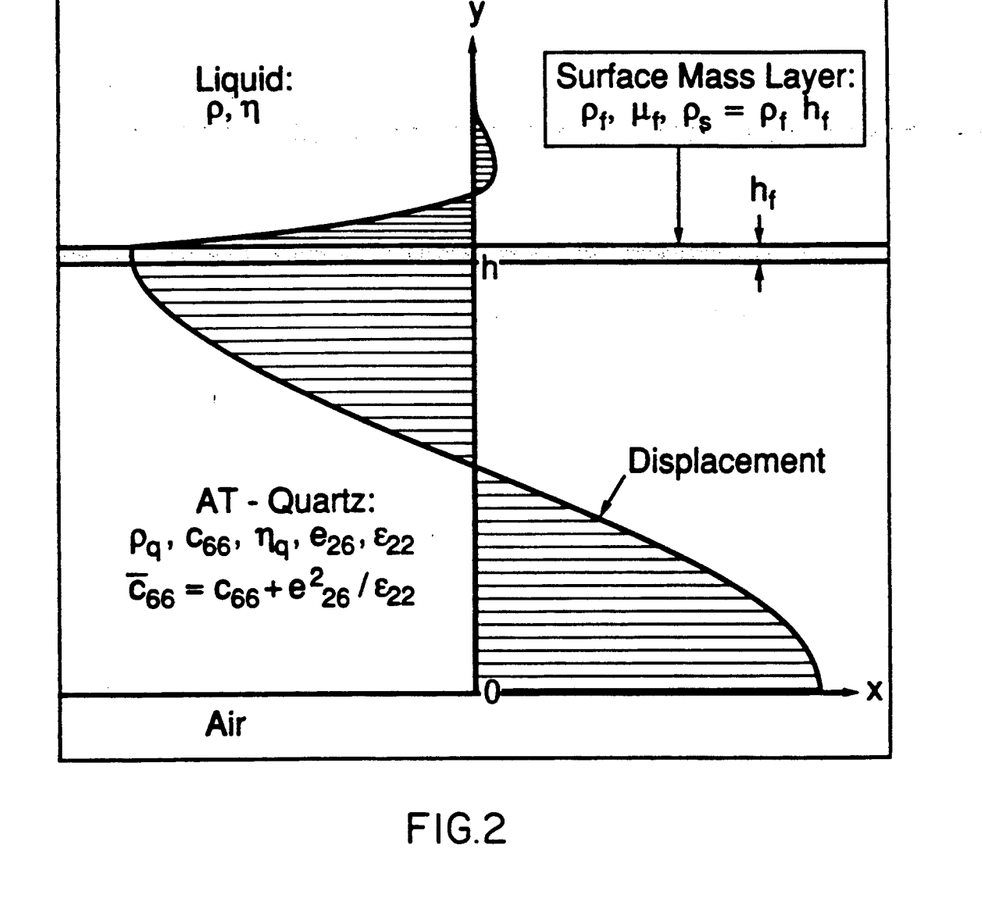
FIG. 2 is a cross-sectional view of a QCM simultaneously loaded on one side by a surface mass layer and a contacting fluid.

FIG. 1 depicts the cross-sectional geometry of the QCM 10 loaded from above by a surface mass layer 20 and a contacting fluid 22. Excitation electrodes 24 and 26 are also located at the upper and lower quartz surfaces, 28 and 30, respectively. The mass layer 20 is on top of the QCM 10 and may or may not be derived from the contacting fluid 22. The mass layer 20 is thin compared to the acoustic wavelength, it is solid and rigidly attached to the QCM 10, ensuring synchronous motion with the oscillating surface. The mass layer 20 may be, for example, metals, metal alloys, salts, some rigid polymers, or ice. The mass layer 20 may be applied to the QCM 10 by evaporation, electroplating, precipitation, or other chemical or thermodynamic reaction. When the contacting fluid 22 contacts this oscillating surface, a damped shear wave is radiated into the fluid, as shown in FIG. 2. QCM surface displacement causes synchronous motion of the surface mass layer and entrainment of the contacting fluid. As long as the fluid thickness is large compared to the decay length of the radiated shear wave, the fluid may be considered semi-infinite.

Coupling between mechanical displacement and electrical potential in the piezoelectric quartz causes mechanical interactions between the QCM and contacting media to influence the electrical characteristics of the QCM, particularly near resonance, where the amplitude of crystal oscillation is greatest. The QCM electrical characteristics can be evaluated using the electrical *admittance*. Admittance is defined as the ratio of current flow to applied voltage, and may be considered to be the reciprocal of impedance. This parameter contains information about the energy stored and the power dissipated in both the QCM and the perturbing media. The admittance of the QCM is obtained by solving a boundary-value problem that includes the mass layer and contacting fluid.

Figure 3:
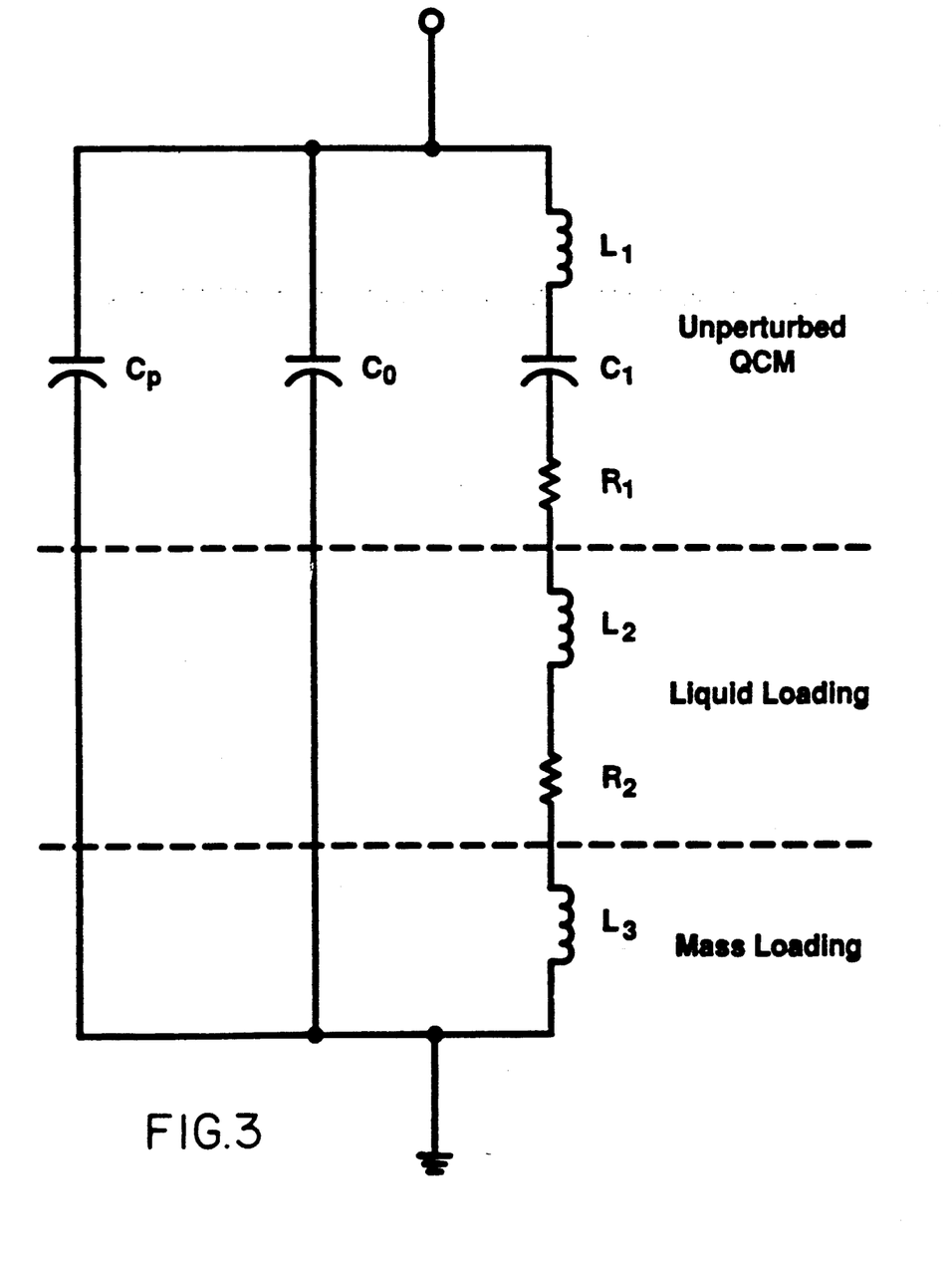
FIG. 3 shows the equivalent circuit for a QCM under mass and liquid loading.

FIG. 3 shows an equivalent circuit model that describes the electrical admittance of the QCM simultaneously loaded by mass and a contacting liquid. The impedance elements in the equivalent circuit model can be related to the properties of the QCM, the mass layer, and the contacting liquid. The current flow out of the lower electrode and into the upper electrode is known.

Thus, the QCM admittance can be described in terms of its physical properties, surface mass layer, and contacting fluid.

The method of the invention described herein involves characterizing the unperturbed QCM and comparing the differences of those characterizations after the QCM has been loaded with mass and/or liquid. An interesting feature is that the elements that arise from mass and fluid loading are related to the unperturbed QCM parameters. The parasitic capacitance, $C_p$, depends upon the geometry of the test fixture and the QCM electrode patterns. The static capacitance, $C_o$, arises from internal fields across the quartz, which also excite the mechanical response of the QCM, but $C_p$ arises from fields external to the QCM. Therefore, by measuring the resonance and broadband admittance characteristics, $C_o$ can be separated from $C_p$. The total admittance, Y, can be found from an inspection of the equivalent circuit model and, including the parasitic contribution $C_p$, where $Z_m$ is the motional impedance, is:

$$Y = j\omega(C_o + C_p) + 1/Z_m$$

This equation assumes that the mass and fluid are contacting only a single side of the QCM; for two-sided contact, certain resistive and motional inductance factors are doubled and the conduction current between electrodes must be considered.

The influence of the mass and fluid perturbations arise from a change in QCM stored energy caused by the perturbation, i.e., resulting from the kinetic energy of the bound mass and/or entrained fluid layer, and the power dissipation because of the radiation of a damped shear wave into the fluid by the oscillating QCM surface, but moving mass does not cause power dissipation. Fluid loading causes an increase in both the motional inductance as well as resistance. In contrast, mass loading increases only the motional inductance.

It has also been determined from the analysis that the effect of mass and fluid loading on charging the resonant frequency is additive and that it is impossible to differentiate changes in surface mass from fluid properties when monitoring only the resonant frequency. The maximum admittance, $Y_{max}$, is affected by fluid loading, with the maximum admittance diminishing with $\rho\eta$ where $\rho$ and $\eta$ are fluid density and viscosity, respectively, but is unaffected by surface mass areal $\rho_s$. When the unperturbed QCM has been fully characterized, $\rho_s$ and $\rho\eta$ can be simultaneously determined from measurements of $\Delta f_s$ and $Y_{max}$. Moreover, QCM sensitivity to surface mass can be emphasized over fluid sensitivity by operating at a higher harmonic.

The quartz crystals are 2.54 cm diameter, synthetic AT-cut quartz wafers, and those skilled in the art will understand that other crystalline cuts of quartz, as well as lithium niobate, and certain cuts of lithium tantalate, or any piezoelectric material that allows shear deformations to be electrically excited may be used. The QCMs, nominally 0.33 mm thick, have planar faces that preferably should be lapped and polished. An electrode pattern may be formed by any number of means, including vacuum-evaporating a chromium adhesion layer, followed by a gold layer. The QCM electrode geometry contains a grounded electrode on one side, while the other side contains an electrode at RF potential. Because the electric field is largely confined to the quartz region beneath the smaller electrode, the QCM active area is approximately this smaller electrode area. The larger electrode is contacted by a metal strip that wraps around the right edge of the QCM enabling both electrodes to be contacted from one side, but other contacting methods including two-sided contacts also may be used.

The surface smoothness of the QCMs is critical for obtaining useful admittance measurements. Smoothness is quantified by a measurement of average surface roughness ($R_a$) using a profilometer. Commercial QCMs have a wide range of $R_a$ values (0.01 to 0.35 μm). It is preferable, however, that the QCM used in the invention have a required $R_a \leq 0.1$ μm. It appears that when surface features are small compared to the fluid decay length ($\delta = 0.15$-$1.8$ μm with fluids tested), the surface behaves as an ideal shear plane interacting with the fluid. Otherwise, alternate mechanisms, such as compressional wave generation, exist for coupling energy from the QCM into the fluid which leads to erroneous results. The QCM roughness leads to increased mass loading because of fluid entrainment and increased dissipation. This results in increased inductance and resistance.

To make electrical measurements, the QCM was mounted in an aluminum RF test fixture, although other test fixtures may be configured to permit, for instance, the fluid to flow across the device. The fixture allows an RF connector to be soldered directly to the smaller electrode and a ground connection to be soldered to the larger electrode. A solder consisting of 1:1 Pb:In may be used to avoid amalgamation and removal of the gold electrode. Pressure contact alone typically resulted in parasitic contact resistance and capacitance, precluding the fitting of measured admittance data to an equivalent circuit. The aluminum fixture has an opening which permits fluid to contact the grounded electrode of the QCM. Immersing the larger electrode in the fluid and keeping that electrode at ground potential prevents fringing RF fields from entering the fluid and causing electrochemical processes and acoustoelectric interactions. It may be necessary to form a fluid seal between the quartz and the test fixture. The QCM test fixture may also be temperature regulated.

A network analyzer measured the complex scattering parameter $S_{11}$, i.e., reflection magnitude and phase, from which admittance spectra are determined. Measurements were made at multiple points centered about the fundamental and third harmonic resonant frequencies of the dry QCM. To characterize the unloaded QCM at its fundamental resonance, a scan was made over a limited bandwidth to capture the sharp resonance peak, as well as over a bandwidth range to capture the broad-band characteristics. To characterize the unloaded QCM at the third harmonic resonance, scans are also made over limited and broad bandwidths. An incident RF power is applied and the frequencies are scanned. Each measured $S_{11}$ value was converted to a complex admittance, Y, using the relation:

$$Y(f) = \frac{1}{Z_o} \frac{1 - S_{11}(f)}{1 + S_{11}(f)}$$

where $Z_o$ is the characteristic impedance of the measurement system. The admittance, Y, can be decomposed into real and imaginary parts ($Y = Y_r + jY_i$), from which the admittance magnitude $|Y|$ and phase angle $\angle Y$ are obtained:

$$|Y| = (Y_r^2 + Y_i^2)^{\frac{1}{2}}$$

$$\angle Y = \tan^{-1}(Y_i/Y_r)$$

For a typical unperturbed QCM in air, the series resonance $f_s$ is defined as when $|Y|$ is maximum and $\angle Y$ is zero. Parallel resonance $f_p$ occurs when $|Y|$ is minimum and $\angle Y$ is zero. The parameters related to extrinsic QCM properties, i.e., dependent upon QCM geometry, such as thickness h and area A), are determined. The intrinsic properties of the AT-cut quartz are: $\rho_q = 2.651$ g/cm$^3$, $\bar{c}_{66} = 2.947 \times 10^{11}$ dyne/cm$^2$, $K^2 = 7.74 \times 10^{-3}$, and $\eta_q = 3.5 \times 10^{-3}$ g/cm−s. The QCM operated in air is nearly unperturbed, but has a small resistive and inductive contribution because of the non-zero density and viscosity of air.

The invention actually contemplates two methods of obtaining admittance/frequency data. The first method would be to apply an oscillating signal to the QCM at its resonant frequency, and then while oscillating at the resonant frequency, measure the magnitude of the admittance of the QCM. When the mass and/or liquid loading is added, the resonant frequency and maximum admittance are remeasured. From the change in resonant frequency, $\Delta f$, and loaded maximum admittance magnitude, $Y_{max}$, we can simultaneously determine the surface mass density $\rho_2$ and contacting liquid density-viscosity product, $\rho\eta$. This model assumes an "ideal" mass layer that has infinitesimal thickness and stiffness, a condition that is approximated in a number of circumstances. According to the model, the resonant frequency depends on a linear combination of mass and liquid loading terms, while the peak admittance depends only on the liquid loading:

$$\Delta f = \frac{-\omega_o}{2N\pi^2 k_1 \bar{c}_{66}} \left[ \omega_o^2 \rho_s + \omega_o \sqrt{\frac{\omega_o \rho \eta}{2}} \right]$$

$$\frac{1}{Y_{max}} = \frac{c_{66}''}{\omega_o C_o K^2 c_{66}'} + \frac{N\pi}{4\sqrt{2K^2}\, C_o} \sqrt{\frac{\rho\eta}{c_{66}\rho Q \omega_o}} = Z_{min}$$

These equations can be solved for surface mass density, $\rho_s = \rho_f h$, where $\rho_f$ and $h$ are the density and thickness of the mass layer, and the liquid density-viscosity product $\rho\eta$, where $\omega_o$ is the angular frequency of $2\pi f$, N is the harmonic number, the $c_{66}$ factors are quartz stiffness parameters, $K^2$ is an electromechanical coupling factor, $\rho_Q$ is the quartz density and $k_1$ is the wavenumber which is related to the thickness of the quartz:

$$\rho\eta = \frac{\left[ Z_{min} - \frac{c_{66}''}{\omega_o C_o K^2 c_{66}'} \right]^2 32 K^4 C_o^2 \bar{c}_{66} \rho_Q \omega_o}{N^2 \pi^2}$$

$$\rho_s = \frac{-\Delta f 2N\pi^2 k_1 c_{66}}{\omega_o^3} - \frac{4K^2 C_o \sqrt{\bar{c}_{66}\rho_Q}}{N\pi} \left[ Z_{min} - \frac{c_{66}''}{\omega_o C_o K^2 c_{66}'} \right]$$

Therefore, a measurement of the change in resonant frequency and the admittance at resonance can be used to extract the surface mass density, $\rho_s$, and the viscosity-density product, $\rho\eta$, of the solution. This result, showing how the surface mass and liquid properties can be obtained from the resonant frequency and the admittance, is a crucial part of the technique and has not been previously demonstrated.

A second method contemplates measuring the phase and magnitude of admittance over a frequency range centered around a fundamental or harmonic resonant frequency of the QCM. The data is then fit to the equivalent circuit model of FIG. 3. Fitting the admittance/frequency data to the model allows for determination of equivalent circuit parameters which in turn can be correlated to obtain a solid mass accumulation and the density-viscosity product. A complete theoretical analysis and solution of the boundary value problem for the admittance within a QCM contacting a solid mass layer and a fluid is given in Martin et al., "Characterization of a Quartz Crystal Microbalance with Simultaneous Mass and Liquid Loading," *ANAL. CHEM.*, Vol. 63, No. 20, pp. 2272-2281 Oct. 15, 1991), which is hereby incorporated by reference.

It is to be appreciated that either of the two methods above may be used to measure either the solid mass accumulation and the liquid properties; or both simultaneously. For example, if no solid mass accumulates onto the surface of the QCM, then an accurate measurement of the density-viscosity product is obtained. And if the properties of the fluid do not change or if there is no fluid contacting the QCM, solid mass accumulation may be measured.

Figure 4:
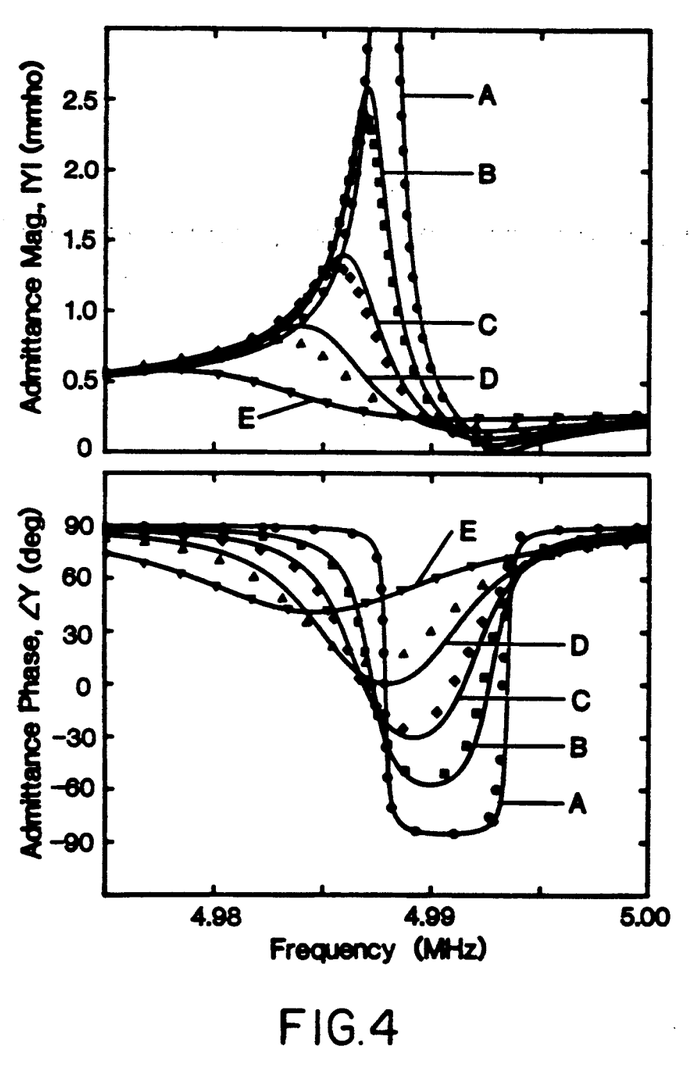
FIG. 4 shows QCM admittance measured (points) and calculated (lines) near the fundamental resonance as the density-viscosity product ($\rho\eta$, $g^2/cm^4-s$) of a contacting fluid increases.

To measure the effect of viscous loading on QCM admittance, various solutions contacted the grounded side of the QCM. The solutions were distilled water and three glycerol/water mixtures having distinct viscosity-density products. FIG. 4 shows admittance and frequency data (points) measured at the fundamental resonance as solution properties alone were changed. Several glycerol/water mixtures of varying density $\rho$ and viscosity $\eta$ contacted the device: (A) air, $\rho\eta = 2 \times 10^{-7}$; (B) water, $\rho\eta = 0.010$; (C) 43% glycerol in H$_2$O, $\rho\eta = 0.044$; (D) 64% glycerol in H$_2$O, $\rho\eta = 0.15$; (E) 80% glycerol in H$_2$O, $\rho\eta = 0.72$. With increasing $\rho\eta$, the admittance magnitude plot shows both a translation of the series resonance peak toward lower frequency, as well as a diminution and broadening of the peak. The parallel or anti-resonant dip in $|Y|$ also becomes less pronounced as $\rho\eta$ increases. The admittance phase plot indicates that phase shifts occurring at $f_s$ and $f_p$ become less sharp and begin to cancel each other as $\rho\eta$ increases.

The translation of the admittance curves arises from the inductance contribution which represents the kinetic energy of the entrained fluid layer. The broadening and diminution of the resonance peaks arises from the resistance contribution; this element may be called a "radiation resistance" because it represents power dissipation arising from the radiation of a shear wave into the fluid by the oscillating QCM surface. Increasing $\rho\eta$ causes a proportional increase in both energy storage and power dissipation.

Figure 5:
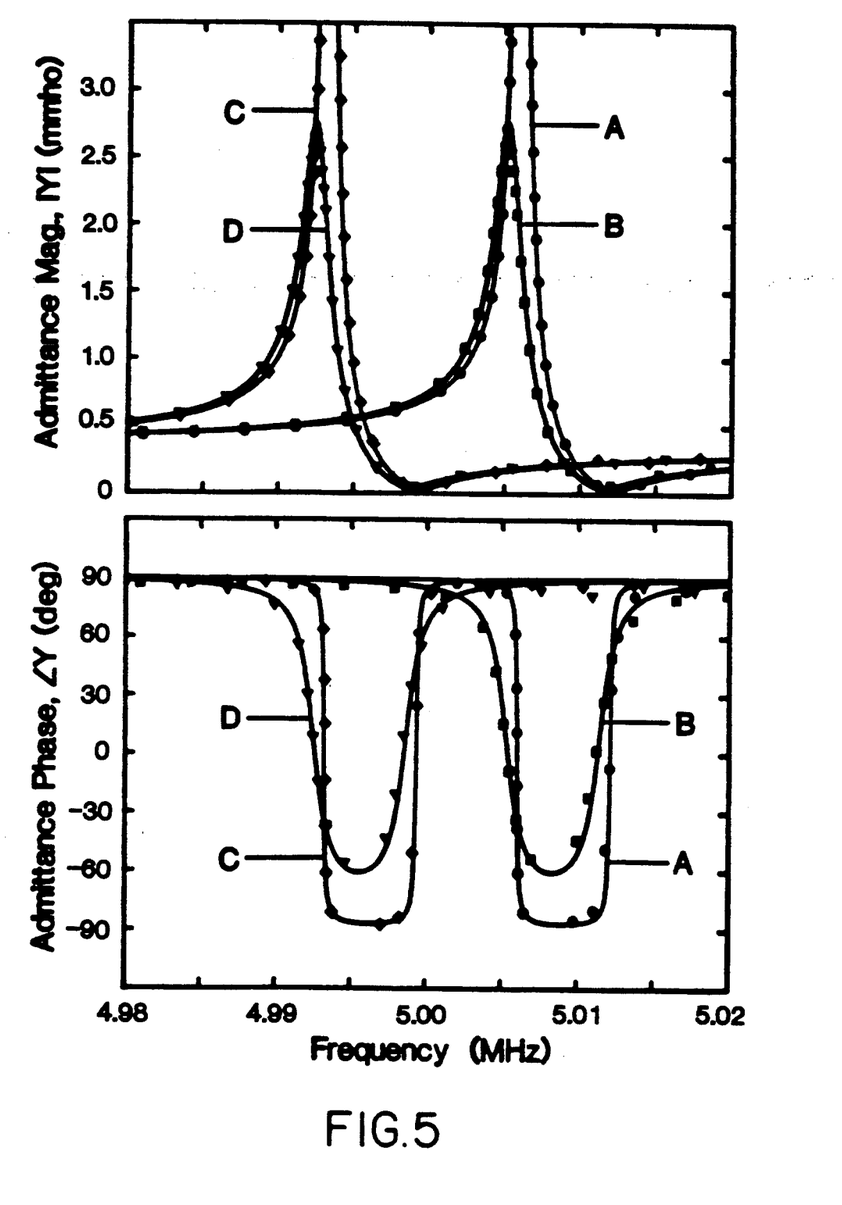
FIG. 5 shows the QCM admittances measured (points) and calculated (lines) before and after deposition of a thin layer of gold.

To measure the effect of surface mass on QCM admittance, measurements were made before and after the vacuum deposition of a gold film. The gold film was evaporated onto the larger electrode to provide a thin adherent mass layer. The gold thickness was determined from profilometry to be 124 nm. FIG. 5 shows the effect of mass loading on QCM admittance near the fundamental resonance: (A) in air before deposition; (B) in water before deposition; (C) in air after deposition; and (D) in water after deposition of a 124 nm gold layer.

It is apparent that the major effect of mass deposition is to translate the admittance curves toward lower frequency without affecting the admittance magnitude. The increased kinetic energy contributed by the mass layer moving synchronously with the QCM surface, and the solid lines in FIG. 5 are predicted admittances. The result of calculations corresponds to a surface mass density $\rho_s = 225$ $\mu$g/cm$^2$. Using the bulk density of gold at 19.30 g/cm$^3$, this surface mass density corresponds to a gold thickness of 117 nm, which is within 6% of the thickness determined from profilometry measurements (124 nm). Thus, electrical admittance measurements can be related directly to mass accumulation on the QCM.

In summary, an analytic expression for the admittance of a QCM simultaneously loaded by a thin mass layer and/or contacting fluid has been derived. Mass and fluid loading lead to distinct admittance/frequency curves that can be used to discriminate between these loading mechanisms. This capability provides for important QCM applications such as fluid phase chemical sensors, viscometers, and plating rate monitors. The measurement of $\Delta f$ and $Y_{max}$ is sufficient to determine $\rho_s$ and $\rho\eta$; these parameters can be extracted from a QCM oscillator circuit having automatic gain control. However, the nature of the admittance/frequency data leads to greater precision in determining $\rho_s$ and $\rho\eta$, particularly at high $\rho\eta$, where the resonance peak is very broad.

The method of the invention herein has applications in the field of electroless and electrolytic plating, and permits the real-time monitoring of the plating rate and solution specific gravity. Because the specific gravity of the plating solution can increase with time, particularly if the plating bath is overstabilized, it is extremely beneficial to monitor both the plating rate to ensure that the plating thickness is adequate and that the process is in control, and the specific gravity to determine that the mass measurements are accurate.

The invention is also useful in sensor applications where an analyte is deposited as a mass layer onto a substrate from a contacting solution. Real-time-in-situ sol-gel viscosity measurements can now be accomplished economically because only the very thin layer of fluid contacting the QCM will be affected, leaving the bulk fluid unperturbed.

While the invention has been described with respect to several embodiments, and to several applications, it is intended that the invention not be limited to the specifics disclosed therein; rather, the invention is presented as broadly claimed.

What is claimed is:

1. A method to determine total mass of a solid and physical properties of a fluid, contacting the same quartz crystal microbalance, comprising:
   (a) applying an oscillating electric field across the thickness of said quartz crystal microbalance;
   (b) measuring at least one resonant frequency of said quartz crystal microbalance;
   (c) simultaneously measuring the admittance magnitude at said resonant frequencies to characterize an unperturbed state;
   (d) applying a solid mass and a fluid onto said quartz crystal microbalance where said quartz crystal microbalance is in contact with said solid mass interposed between said quartz crystal microbalance and said fluid to produce a perturbed state;
   (e) measuring at least one resonant frequency of said quartz crystal microbalance in said perturbed state;

(f) simultaneously measuring the admittance magnitude of said quartz crystal microbalance in said perturbed state;

(g) correlating changes in said resonant frequencies and changes in said admittance magnitudes of said unperturbed states to obtain a surface mass density and a fluid viscosity-density product.

2. The method of claim 1, wherein said resonant frequency is a fundamental frequency.

3. The method of claim 1, wherein said resonant frequency is a fundamental and a harmonic frequency.

4. A method to determine total mass contacting a quartz crystal microbalance comprising:

(a) applying an oscillating electric field across the thickness of said quartz crystal microbalance;

(b) measuring at least one resonant frequency of said quartz crystal microbalance;

(c) simultaneously measuring the admittance magnitude at said resonant frequencies to characterize an unperturbed state;

(d) applying a solid mass onto said quartz crystal microbalance where said quartz crystal microbalance is in contact with said solid mass to produce a perturbed state;

(e) measuring at least one resonant frequency of said quartz crystal microbalance in said perturbed state;

(f) simultaneously measuring the admittance magnitude of said quartz crystal microbalance in said perturbed state;

(g) correlating changes in said resonant frequencies and changes in said admittance magnitudes of said unperturbed and perturbed states to obtain a surface mass density.

5. A method to determine physical properties of a fluid contacting a quartz crystal microbalance, comprising:

(a) applying an oscillating electric field across the thickness of said quartz crystal microbalance;

(b) measuring at least one resonant frequency of said quartz crystal microbalance;

(c) simultaneously measuring the admittance magnitude at said resonant frequencies to characterize an unperturbed state;

(d) applying a fluid onto said quartz crystal microbalance where said quartz crystal microbalance is in contact with said fluid to produce a perturbed state;

(e) measuring at least one resonant frequency of said quartz crystal microbalance in said perturbed state;

(f) simultaneously measuring the admittance magnitude of said quartz crystal microbalance in said perturbed state;

(g) correlating changes in said resonant frequencies and changes in said admittance magnitudes of said unperturbed and perturbed states to obtain a fluid viscosity-density product.

6. A method to determine total mass contacting a quartz crystal microbalance, and physical properties of a fluid in contacting said quartz crystal microbalance, comprising:

(a) applying a series of oscillating electric fields of varying frequency across the thickness of said quartz crystal microbalance where said field frequencies are over a range which spans at least one resonant frequency of said crystal;

(b) measuring the magnitude and phase of the admittance over said frequency range;

(c) correlating said admittance data to said frequency, and fitting said admittance and said frequency data to and equivalent circuit model to characterize and unperturbed QCM state;

(d) contacting a solid mass and a fluid onto said crystal, said solid mass interposed between said crystal and said fluid;

(e) repeating steps (b) and (c);

(f) correlating said admittance data to said frequency, and fitting said admittance and said frequency data to an equivalent circuit model to characterize an perturbed QCM state;

(g) extracting solid mass and fluid density-viscosity product from relating said characterized data of said QCM in unperturbed and perturbed states.

7. A method to determine physical properties of a fluid contacting said quartz crystal microbalance, comprising:

(a) applying a series of oscillating electric fields of varying frequency across the thickness of said quartz crystal microbalance where said field frequencies are over a range which spans at least one resonant frequency of said crystal;

(b) measuring the magnitude and phase of the admittance over said frequency range;

(c) correlating said admittance data to said frequency, and applying said admittance/frequency correlation to an equivalent circuit model to characterize an unperturbed QCM state;

(d) contacting a fluid onto said crystal;

(e) repeating steps (b) and (c);

(f) correlating said admittance data to said frequency, and applying said admittance/frequency correlation to an equivalent circuit model to characterize a perturbed QCM state;

(g) extracting fluid density-viscosity product from said correlated admittance and said frequency data from said unperturbed and said perturbed QCM states.

8. A method to determine total solid mass contacting a quartz crystal microbalance, comprising:

(a) applying a series of oscillating electric fields of varying frequency across the thickness of said quartz crystal microbalance where said field frequencies are over a range which spans at least one resonant frequency of said crystal;

(b) measuring the magnitude and phase of the admittance over said frequency range;

(c) correlating said admittance data to said frequency, and applying said admittance/frequency correlation to an equivalent circuit model to characterize an unperturbed QCM state;

(d) contacting a mass onto said crystal, and solid mass oscillating synchronously with said crystal;

(e) repeating steps (b) and (c);

(f) correlating said admittance data to said frequency, and applying said admittance/frequency correlation to an equivalent circuit model to characterize a perturbed QCM state;

(g) extracting solid mass from said correlated admittance and said frequency data from said unperturbed and said perturbed QCM states.

* * * * *